US010265253B2

(12) United States Patent
Klug et al.

(10) Patent No.: US 10,265,253 B2
(45) Date of Patent: Apr. 23, 2019

(54) N-METHYL-N-ACYLGLUCAMINE-CONTAINING COMPOSITION

(71) Applicant: Clariant International Ltd., Muttenz (CH)

(72) Inventors: Peter Klug, Grossostheim (DE); Carina Mildner, Frankfurt am Main (DE)

(73) Assignee: Clariant International Ltd., Muttenz (CH)

(*) Notice: Subject to any disclaimer, the term of this patent is extended or adjusted under 35 U.S.C. 154(b) by 0 days.

(21) Appl. No.: 14/401,323

(22) PCT Filed: May 29, 2013

(86) PCT No.: PCT/EP2013/061075
§ 371 (c)(1),
(2) Date: Nov. 14, 2014

(87) PCT Pub. No.: WO2013/178683
PCT Pub. Date: Dec. 5, 2013

(65) Prior Publication Data
US 2015/0141508 A1   May 21, 2015

(30) Foreign Application Priority Data
May 30, 2012 (DE) .................. 10 2012 010 656

(51) Int. Cl.
| | |
|---|---|
| *A61K 8/41* | (2006.01) |
| *A61K 8/42* | (2006.01) |
| *A61K 8/44* | (2006.01) |
| *A61K 8/46* | (2006.01) |
| *A61Q 5/02* | (2006.01) |
| *A61Q 19/10* | (2006.01) |
| *A61K 8/92* | (2006.01) |
| *C11D 1/94* | (2006.01) |
| *C11D 3/20* | (2006.01) |
| *C11D 3/43* | (2006.01) |
| *A61K 8/37* | (2006.01) |
| *C11D 1/02* | (2006.01) |
| *C11D 1/14* | (2006.01) |

(52) U.S. Cl.
CPC .................. *A61K 8/42* (2013.01); *A61K 8/37* (2013.01); *A61K 8/41* (2013.01); *A61K 8/442* (2013.01); *A61K 8/463* (2013.01); *A61K 8/922* (2013.01); *A61Q 5/02* (2013.01); *A61Q 19/10* (2013.01); *C11D 1/94* (2013.01); *C11D 3/2093* (2013.01); *C11D 3/43* (2013.01); *A61K 2800/262* (2013.01); *C11D 1/02* (2013.01); *C11D 1/14* (2013.01)

(58) Field of Classification Search
CPC .......... A61K 2800/10; A61K 2800/596; A61K 8/345; A61K 8/41; A61K 8/42; A61K 8/463
See application file for complete search history.

(56) References Cited

U.S. PATENT DOCUMENTS

| | | |
|---|---|---|
| 2,703,798 A | 3/1955 | Schwartz |
| 5,317,047 A | 5/1994 | Sabate et al. |
| 5,454,982 A * | 10/1995 | Murch .................. C11D 1/525 510/300 |
| 7,820,771 B2 | 10/2010 | Lapra et al. |
| 8,729,323 B2 * | 5/2014 | Kothandaraman ..... C07C 1/323 44/605 |
| 2014/0303389 A1* | 10/2014 | Crosby ................ C12P 7/6454 554/227 |
| 2015/0125415 A1 | 5/2015 | Klug et al. |
| 2015/0126424 A1 | 5/2015 | Klug et al. |
| 2015/0126616 A1 | 5/2015 | Klug et al. |
| 2015/0133560 A1 | 5/2015 | Klug et al. |
| 2015/0140048 A1 | 5/2015 | Klug et al. |
| 2015/0141466 A1 | 5/2015 | Klug et al. |
| 2015/0150767 A1 | 6/2015 | Klug et al. |
| 2015/0164755 A1 | 6/2015 | Klug et al. |
| 2015/0164756 A1 | 6/2015 | Klug et al. |
| 2015/0320037 A1 | 11/2015 | Wacker |
| 2016/0074310 A1 | 3/2016 | Klug et al. |
| 2016/0136072 A1 | 5/2016 | Klug et al. |
| 2016/0143828 A1 | 5/2016 | Klug et al. |

(Continued)

FOREIGN PATENT DOCUMENTS

| | | |
|---|---|---|
| EP | 0550637 | 7/1993 |
| EP | 1 078 978 | 2/2001 |

(Continued)

OTHER PUBLICATIONS

Plante et al. Castor Oil [online] retrieved on Jan. 13, 2016 from: http://www.dionex.com/en-us/webdocs/110518-PO-UHPLC-Castor-Oil-31May2011-LPN2822-01.pdf; 5 pages.*
Bezard (Lipids 1971;6:630-634).*
Skrypzak et al. (English translation of EP1078978A1) Feb. 28, 2001; 8 pages.*
Tan et al. (Appl Microbiol Biotechnol. 1997;47:207-211) (Year: 1997).*
Dale et al. (J. Sci. Food. Agric. 1955;6:166-170) (Year: 1955).*
Palm fatty acid distillate (PFAD) [online] retrieved on May 21, 2018 from: https://www.neste.com/corporate-info/sustainability/sustainable-supply-chain/pfad-residue-palm-oil-refining-process; 1 page (Year: 2018).*
Hardcopy of http://igf-bingen.de/Croda_produkte.pdf, Dec. 1, 2016.
English abstract for EP 1 078 978, Feb. 28, 2001.
International Search Report for PCT/EP2013/061075, dated May 15, 2014.

*Primary Examiner* — Ernst V Arnold
(74) *Attorney, Agent, or Firm* — Tod A. Waldrop

(57) ABSTRACT

The invention relates to a clear composition which contains at least one anionic surfactant, a betaine surfactant, an N-methyl-N-acylglucamine, a triglyceride oil, a solvent and optionally an additive. The invention also relates to a method for producing the composition. The invention further relates to the use of the composition for the treatment or care of skin or hair, or for use as a shampoo, face cleaner, liquid cleaner or shower gel.

15 Claims, No Drawings

(56) References Cited

U.S. PATENT DOCUMENTS

| | | | |
|---|---|---|---|
| 2016/0243014 A1 | 8/2016 | Dahms et al. |
| 2016/0272666 A1 | 9/2016 | Klug et al. |
| 2016/0361243 A1 | 12/2016 | Klug et al. |
| 2017/0000710 A1 | 1/2017 | Klug et al. |
| 2017/0002297 A1 | 1/2017 | Klug et al. |
| 2017/0044434 A1 | 2/2017 | Baur et al. |
| 2017/0055524 A1 | 3/2017 | Baur et al. |
| 2017/0071199 A1 | 3/2017 | Baur et al. |
| 2017/0101606 A1 | 4/2017 | Klug et al. |
| 2017/0218293 A1 | 8/2017 | Klug et al. |
| 2017/0265477 A1 | 9/2017 | Baur et al. |
| 2017/0292062 A1 | 10/2017 | Wylde et al. |
| 2017/0305838 A1 | 10/2017 | Appel et al. |
| 2018/0215879 A1 | 8/2018 | Soeffing et al. |

FOREIGN PATENT DOCUMENTS

| | | |
|---|---|---|
| WO | WO 92/06158 | 4/1992 |
| WO | WO 92/06161 | 4/1992 |
| WO | WO 93/19149 | 9/1993 |
| WO | WO 95/17880 | 7/1995 |
| WO | WO 96/03974 | 2/1996 |
| WO | WO 96/37592 | 11/1996 |
| WO | WO 2016/041823 | 3/2016 |

\* cited by examiner

N-METHYL-N-ACYLGLUCAMINE-CONTAINING COMPOSITION

The invention relates to a composition containing at least one anionic surfactant, a betaine surfactant, an N-methyl-N-acylglucamine, a triglyceride oil, a solvent and if desired an additive, and also a process for producing the composition. The invention further relates to the use of the composition for treatment or care of the skin or hair or as shampoo, face cleanser, liquid cleanser or shower gel.

In the production of compositions, in particular for the production of cleansing compositions, attention should be paid to a number of criteria such as good cleansing action, sufficient foaming properties, good skin compatibility and a good feel when used on skin and hair and especially no irritation of the mucous membranes. Skin and hair consist of a plurality of layers which comprise, inter alia, keratin and collagen as fiber proteins. Anionic surfactants can penetrate into the layers and destroy these. Ideal cosmetic cleansers for cosmetic or pharmaceutical applications should cleanse the skin or hair gently without oil/fat removal from and/or drying of the hair and the skin and without causing irritation.

In the production of cosmetic or dermatological preparations, the problem that particular constituents, in particular care components such as cosmetic oils, do not have sufficient solubility in water and the preparations become turbid or form a plurality of phases, in particular in the presence of salts, frequently arises.

WO 95/17880 relates to shampoo compositions having functional materials as conditioning agents, styling aids or antidandruff agents. In the text, a light, readily foaming shampoo composition having high deposition of functional materials is provided, where the shampoo composition comprises: (a) from about 5% to about 40% of surfactant comprising: (i) from 80% to about 99%, based on the surfactant system, of anionic surfactants which are alkyl-ethoxylated sulfates and alkylsulfates in a ratio of from about 1:1 to 1:0, and (ii) about from about 1% to 20%, based on the surfactant system, of polyhydroxy fatty acid amide surfactants, (b) from about 0.05% to about 25% by weight of functional materials and (c) from about 35% to about 95% by weight of water.

WO 96/37592 describes a mild, foam-producing cleansing product for cleansing the skin or hair, with this being able to be used as bubble bath and shower product, skin cleanser and shampoo. According to one aspect of this document, a detergent, cleanser or cosmetic composition comprising: (a) from about 1% to about 25% of water-soluble gel which forms a nonionic surfactant; (b) from about 0.1% to about 3% by weight of an alkylsulfate which acts as fluidizer and has on average from 4 to 10 carbon atoms in the alkyl chain; and (c) if desired from about 1% to about 30% by weight of a dispersed oil phase is provided. The surfactants form homogeneous (opaque) product matrices in which the oil droplets have a diameter in the range from about 1 micron to about 30 microns.

The document WO 92/06158 relates to a low-foam detergent composition comprising at least 1% by weight of a polyhydroxy fatty acid amide surfactant of the formula

where $R^1$ is H, $C_1$-$C_4$-hydrocarbon, 2-hydroxyethyl or 2-hydroxypropyl, $R^2$ is $C_5$-$C_{31}$-hydrocarbon and Z is a polyhydroxyhydrocarbon having a linear hydrocarbon chain having at least three hydroxyl groups bound directly to the chain or alkoxylated derivatives thereof; at least 1% of an alkyl-alkoxylated sulfate surfactant; and if desired a foam-suppressing amount of an antifoam selected from the group consisting of monocarboxylic fatty acids and salts thereof, silicone antifoams and monostearyl alkali metal phosphates or phosphate esters and high molecular weight hydrocarbon antifoams and mixtures thereof; where the composition has an alkyl-alkoxylated sulfate:polyhydroxy fatty acid amide weight ratio of from 10:1 to 1:10, preferably from 5:1 to 1:5 and more preferably from 4:1 to 1:1 and the polyhydroxy fatty acid amide comprises less than 4% by weight of a cyclic amide by-product.

However, in the formulation of cosmetic compositions, in particular hair care compositions, fatty acid N-alkylglucamides have the disadvantage that their foaming behavior is not always satisfactory. This relates firstly to the height of the base foam and secondly to the foam stability, in particular in hard water. A further disadvantage is that the amides often leave a dull feel on the hair after rinsing off and tend to impair combability.

It is therefore an object of the invention to provide an improved composition which allows large amounts of natural oils as moisturizing substance and is also clear.

The invention accordingly provides a clear composition containing:
  (A) at least one anionic surfactant as component A,
  (B) at least one betaine surfactant as component B,
  (C) at least one N-methyl-N-acylglucamine as component (C), where the N-methyl-N-acylglucamine has a $C_8$-$C_{22}$-acyl radical,
  (D) at least one triglyceride oil as component D,
  (E) at least one solvent as component E and
  (F) if desired one or more additives as component F.

Large amounts of natural oils can be introduced by means the composition of the invention. In addition, the composition does not have to stabilized against separation. Surprisingly, the compositions of the invention have very good foaming despite the presence of triglyceride oils. Compared to conventional ether sulfate/betaine systems or corresponding formulations based on alkyl polyglucoside, the compositions are clear and phase-stable and display good moisturizing performance.

According to the invention, the composition is clear. This means, in particular, that the composition is optically transparent in layer thicknesses of 5 cm and does not appear opaque and emulsion-like as in the case of, for example, compositions from the cited prior art. Furthermore, the compositions do not display any separation into a plurality of phases and are thus homogeneous.

Further names for N-methyl-N-acylglucamine are N-methyl-N-1-deoxy-sorbitol fatty acid amide, N-acyl-N-methylglucamine, glucamide and N-methyl-N-alkylglucamide. Here, N-methyl-N-acylglucamine corresponds to the formula (X), where R is an organic radical:

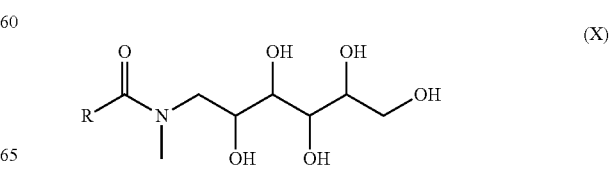

In a preferred embodiment, the component A is selected from among one or more compound(s) of the general formula (I),

  (I)

where $R^1$ is alkyl, cycloalkyl, aralkyl, aryl, alkoxy, alkoxyalkyl or heterocyclyl and M+ is an alkali metal ion, an alkaline earth metal ion or a substituted or unsubstituted ammonium ion, or
of the general formula (II),

  (II)

where $R^1$ is alkyl, cycloalkyl, aralkyl, aryl, alkoxy, alkoxyalkyl or heterocyclyl and M+ is an alkali metal ion, an alkaline earth metal ion or a substituted or unsubstituted ammonium ion.

"Alkyl" is a saturated aliphatic hydrocarbon group which can be linear or branched and can have from 1 to 20 carbon atoms in the chain. Preferred alkyl groups can be linear or branched and have from 1 to 10 carbon atoms in the chain. Branched means that a lower alkyl group such as methyl, ethyl or propyl is present as substituent on a linear alkyl chain. Alkyl is, for example, methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl.

"Cycloalkyl" is an aliphatic ring having from 3 to 10 carbon atoms in the ring. Preferred cycloalkyl groups have from 4 to 7 carbon atoms in the ring.

"Aryl" is phenyl or naphthyl.

"Aralkyl" is an alkyl group substituted by an aryl radical.

"Substituted aralkyl" and "substituted aryl" mean that the aryl group or the alkyl group of the aralkyl group is substituted by one or more substituents selected from among alkyl, alkoxy, nitro, carboalkoxy, cyano, halo, alkylmercaptyl, trihaloalkyl and carboxyalkyl.

"Alkoxy" is an alkyl-O group in which "alkyl" is as defined above. Lower alkoxy groups are preferred. Examples are methoxy, ethoxy, n-propoxy, i-propoxy and n-butoxy.

"Lower alkyl" is an alkyl group having from 1 to 7 carbon atoms.

"Alkoxyalkyl" is an alkyl group as described above which is substituted by alkoxy group as described above. Thus, the term alkoxyalkyl encompasses a polyether.

"Heterocyclyl" is a 4- to 10-membered ring structure in which one or more ring atoms are not carbon, for example are N, O or S. Heterocyclyl can be aromatic or nonaromatic, i.e. it can be saturated, partially or fully unsaturated.

In a preferred embodiment, the anionic surfactant of the component A is an alkylsulfate or an alkyl ether sulfate.

Particular preference is given to sodium laurylsulfate and/or sodium lauryl ether sulfate.

In a preferred embodiment, the component B comprises at least one alkyl betaine and/or at least one alkylamido betaine.

Examples of suitable alkyl betaines are the carboxyalkylation products of amines, in particular secondary and tertiary amines of the formula (III)

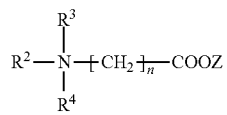  (III)

where $R^2$ is an alkyl and/or alkenyl radical having from 6 to 22 carbon atoms, $R^3$ is hydrogen or an alkyl radical having from 1 to 4 carbon atoms, $R^4$ is hydrogen or an alkyl radical having from 1 to 4 carbon atoms, n is from 1 to 6 and Z is an alkali metal and/or alkaline earth metal or ammonium. Typical examples are the carboxymethylation products of hexylmethylamine, hexyldimethylamine, octyldimethylamine, decyldimethylamine, dodecylmethylamine, dodecyldimethylamine, dodecylethylmethylamine, C12/14-cocoalkyldimethylamine, myristyl-dimethylamine, cetyldimethylamine, stearyldimethylamine, stearylethylmethylamine, oleyldimethylamine, C16/18-tallowalkyldimethylamine and industrial mixtures thereof.

Examples of suitable alkylamido betaines are carboxyalkylation products of amidoamines. Amidopropyl betaines of the formula (IV),

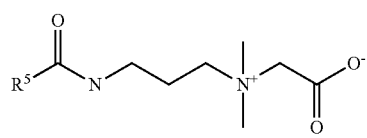  (IV)

where $R^5$ is a linear or branched saturated $C_7C_{21}$-alkyl group or a linear or branched monounsaturated or polyunsaturated $C_7$-$C_{21}$-alkenyl group, are particularly suitable.

Preferred betaine surfactants are amidopropyl betaines such as cocamidopropyl betaine ($R^5CO$ is the fatty acid radical of coconut oil, chain length $C_8$-$C_{18}$) and alkyl betaines such as coco betaine ($R^2$ is the alkyl radical of coconut oil, chain length $C_8$-$C_{18}$) or lauryl betaine ($R^2$ is an alkyl radical having the chain length $C_{12}$ and $C_{14}$).

For the purposes of the invention, a solvent is preferably a protic solvent such as water, a $C_1$-$C_8$-alkyl, in particular $C_1$-$C_6$-alcohols, ethylene glycol, diethylene glycol, triethylene glycol or mixtures thereof, with water and/or ethanol or water and/or methanol being particularly preferred. Among $C_1$-$C_6$-alcohols preference is given to methanol, ethanol, isopropanol, n-butanol or sec-butanol. A preferred solvent is water.

Possible triglycerides are, for example, triglycerides of linear or branched, saturated or unsaturated, hydroxylated or unhydroxylated $C_8$-$C_{30}$-fatty acids, in particular vegetable oils such as sunflower, maize, soybean, rice, jojoba, babassu, pumpkin, grape seed, sesame, walnut, apricot, orange, wheat germ, peach kernel, macadamia, avocado, sweet almond, cuckoo flower, castor, olive, peanut, rapeseed and coconut oil, and also synthetic triglyceride oils, e.g. the commercial product Myritol® 318. Essentially unsaturated triglycerides of vegetable origin such as olive oil are preferred according to the invention. Oils of animal origin, for example beef tallow, perhydrosqualene and lanolin can also be used.

Preference is given to triglycerides which contain $C_8$-$C_{22}$-fatty acids, particularly preferably $C_8$-$C_{18}$-fatty acids, in particular saturated or unsaturated $C_{16}$-$C_{18}$-fatty acids.

Particular preference is given to triglycerides which contain essentially $C_{16}$- and $C_{18}$-fatty acids (known as C16/C18-fatty acids), for example sunflower oil, almond oil and olive oil.

In a preferred embodiment, the composition contains
(A) 5-15% by weight of component A,
(B) 1-4% by weight of component B,
(C) 0.5-5.0% by weight of component C,
(D) 0.01-3.0% by weight of component D,
(E) 5-93.49% by weight of a protic solvent as component E and
(F) 0-10% by weight of component F,
where the sum of the components A to F is 100% by weight.

The composition preferably consists of
(A) 5-15% by weight of component A,
(B) 1-4% by weight of component B,
(C) 0.5-5.0% by weight of component C,
(D) 0.01-3.0% by weight of component D,
(E) 5-93.49% by weight of a protic solvent as component E and
(F) 0-10% by weight of component F,
where the sum of the components A to F is 100% by weight.

A triglyceride oil content of 0.05-2.0% by weight, preferably from 0.1-1.0% by weight and in particular from 0.2-0.6% by weight, is particularly useful, where the sum of all components A to F is 100% by weight.

In a further preferred embodiment, the composition contains (and consists in particular of)
(A) 7.0-10.0% by weight of component A,
(B) 1.5-3.4% by weight of component B,
(C) 1.0-5.0% by weight of component C,
(D) 0.01-3.0% by weight of component D,
(E) 5-90.49% by weight of a protic solvent as component E and
(F) 0-10% by weight of component F,
where the sum of the components A to F is 100% by weight.

In a preferred embodiment, the acyl radical in the component C is selected from the group consisting of linear, branched, saturated or unsaturated $C_8$-$C_{22}$-acyl radicals and mixtures thereof. Particular preference is given to a $C_8$-$C_{18}$-acyl radical. Here, a $C_8$-acyl radical is, for example, an acyl radical derived from octanoic acid.

In a preferred embodiment, the sum of the components A, B and C is 6.5-24.0% by weight, preferably from 10 to 18% by weight and in particular from 11 to 17% by weight.

In a preferred embodiment, the component C consists of a saturated or unsaturated N-methyl-N-acylglucamine or a mixture of a plurality thereof.

In a preferred embodiment, the solvent is water or a mixture of water and propylene glycol.

In a preferred embodiment, the additives are selected from the group consisting of preservatives, fragrances, dyes, further surfactants, water, oil bodies, cationic polymers, film formers, thickeners and gelling agents, oiling agents, antimicrobial and biogenic active compounds, moisture-donating agents, stabilizers, acids, alkalis, activity reinforcers and mixtures thereof, preferably in amounts of from 0.1 to 10.0% by weight, particularly preferably from 0.5 to 8.0% by weight and in particular from 1.0 to 5.0% by weight.

Suitable preservatives are the preservatives listed in the relevant annex of the European cosmetics legislation, for example phenoxyethanol, benzyl alcohol, parabens, benzoic acid and sorbic acid; a particularly well-suited preservative is, for example, 1,3-bis(hydroxymethyl)-5,5-dimethyl-imidazolidine-2,4-dione (Nipaguard® DMDMH).

As fragrances or perfumes or oils, it is possible to use individual fragrance compounds, e.g. the synthetic products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. Ethers include, for example, benzyl ethyl ether, aldehydes include, for example, linear alkanals having from 8 to 18 carbon atoms, citral, citronellal, citronellyloxyacetaldehyde, cyclamen aldehyde, hydroxycitronellal, lilial and bourgeonal, ketones include, for example, ionones, alpha-isomethylionone and methyl cedryl ketone, alcohols include anethole, citronellol, eugenol, geraniol, linalol, phenylethyl alcohol and terpineol, and hydrocarbons include mainly the terpenes and balsams. Preference is given to using various fragrances which together produce a pleasant smell.

Perfume oils can also contain natural fragrance mixtures as can be obtained from vegetable or animal sources, e.g. pine, citrus, jasmine, lily, rose or ylang ylang oil. Ether oils having a low volatility, which are mostly used as aroma components, are also suitable as perfume oils, e.g. sage oil, camomile oil, clove oil, melissa oil, mint oil, cinnamon leaf oil, lime flower oil, juniper berry oil, vetiver oil, olibanum oil, galbanum oil and ladanum oil.

The desired viscosity of the compositions can be set (increased or lowered) by addition of thickeners and gelling agents. Preference is given to cellulose ethers and other cellulose derivatives (e.g. carboxymethylcellulose, hydroxyethylcellulose), gelatin, starch and starch derivatives, sodium alginates, fatty acid polyethylene glycol esters, agar-agar, tragacanth or dextrin derivatives, in particular dextrin esters. Also suitable are metal salts of fatty acids, preferably those having from 12 to 22 carbon atoms, for example sodium stearate, sodium palmitate, sodium laurate, sodium arachidate, sodium behenate, potassium stearate, potassium palmitate, sodium myristate, aluminum monostearate, hydroxy fatty acids, for example 12-hydroxystearic acid, 16-hydroxyhexadecanoic acid; fatty acid amides; fatty acid alkanolamides; dibenzalsorbitol and alcohol-soluble polyamides and polyacrylamides or mixtures of such compounds. It is also possible to use crosslinked and uncrosslinked polyacrylates such as cabomer, sodium polyacrylates or sulfonic acid-containing polymers such as ammonium acryloyldimethyltaurate-carboxyethyl acrylate crosspolymer (Aristoflex TAC®, Clariant).

Sodium chloride is particularly well-suited as thickener.

Antimicrobial active compounds used are, for example, cetyltrimethyl-ammonium chloride, cetylpyridinium chloride, benzethonium chloride, diisobutylethoxyethyldimethylbenzylammonium chloride, sodium N-lauryl-sarcosinate, sodium N-palmethylsarcosinate, lauroylsarcosine, N-myristoyl-glycine, potassium N-laurylsarcosine, trimethylammonium chloride, sodium aluminum chlorohydroxylactate, triethyl citrate, tricetylmethylammonium chloride, 2,4,4'-trichloro-2'-hydroxy(diphenyl ether) (triclosan), phenoxyethanol, 1,5-pentanediol, 1,6-hexanediol, 3,4,4'-trichlorocarbanilide (triclocarban), diaminoalkylamide, for example L-lysine hexadecylamide, heavy metal salts of citric acid, salicylates, piroctoses in particular zinc salts, pyrithiones and heavy metal salts thereof, in particular zinc pyrithione, zinc phenolsulfate, farnesol, ketoconazole, oxyconazole, bifonazoles, butoconazoles, cloconazoles, clotrimazoles, econazoles, enilconazoles, fenticonazoles, isoconazoles, miconazoles, sulconazoles, tioconazoles, fluconazoles, itraconazoles, terconazoles, naftifine and terbinafine, selenium disulfide and octopirox, iodopropynyl butyl carbamate, methylchloroisothiazolinone, methylisothiazolinone, methyldibromoglutaro-nitrile, AgCl, chloroxylenol, Na salt of diethylhexylsulfosuccinate, sodium benzoate and also phenoxyethanol, benzyl alcohol, phenoxyisopropanol, parabens, preferably butylparaben, ethylparaben, methylparaben and propylparaben, and also Na salts thereof, pentanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), Na salt of hydroxymethylglycinate, hydroxyethylglycinate of sorbic acid and combinations of these active compounds.

The compositions of the invention can also contain biogenic active ingredients selected from among plant extracts such as aloe vera, and also local anesthetics, antibiotics, antiphlogistics, antiallergic substances, corticosteroids, sebostatics, Bisabolol®, Allantoin®, Phytantriol®, proteins, vitamins selected from among niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as sodium salt of the monophosphoric ester of ascorbic acid or as magnesium salt of the phosphoric ester of ascorbic acid, tocopherol and tocopherol acetate, and also vitamin E and/or derivatives thereof.

As stabilizers, it is possible to metal salts of fatty acids, e.g. magnesium stearate, aluminum stearate and/or zinc stearate.

Moisture-donating substances available are, for example, isopropyl palmitate, glycerol and/or sorbitol.

As oiling agents, preference is given to using lanolin and lecithin, unethoxylated and polyethoxylated or acylated lanolin and lecithin derivatives, polyol fatty acid esters, monoglycerides, diglycerides and triglycerides and/or fatty acid alkanolamides, with the latter at the same time serving as foam stabilizers.

As acids or alkalis for setting the pH, preference is given to using mineral acids, in particular HCl, inorganic bases, in particular NaOH or KOH, or organic acids, in particular citric acid.

In a preferred embodiment, the composition is a cosmetic, dermatological or pharmaceutical composition.

The invention further provides a process for producing the composition of the invention, which comprises the steps:
a) mixing of the components A and D,
b) addition of the components B and E and subsequent homogenization of the components A, B, D and E,
c) addition of the component C in liquid form and subsequent homogenization of the components A, B, C, D and E,
d) if desired addition of component F and
e) setting of the pH of the composition to 5-8.

The process preferably comprises the abovementioned amounts indicated for the composition of the invention.

The invention further provides for the use of the composition of the invention as shampoo, face cleanser, liquid cleanser or shower gel.

The invention further provides for the use of the composition of the invention for the treatment or care of the skin.

The invention further provides for the use of the composition of the invention for treatment or care of the hair.

The invention is illustrated by the following examples:

PRODUCTION EXAMPLE H1 TO H3, EXAMPLES 1 TO 5 AND ALSO COMPARATIVE EXAMPLES 1 AND 2

The N-acyl-N-methylglucamines described below were prepared from the corresponding methyl esters of fatty acids and N-methylglucamine in the presence of 1,2-propylene glycol as solvent as described in EP 0 550 637 and obtained as a solid consisting of active substance and 1,2-propylene glycol.

C12/14 means that the methyl ester consists of a mixture of methyl laurate ($C_{12}$-acyl radical) and methyl myristate ($C_{14}$-acyl radical) (ratio 75:25).

C8/C14 means that the methyl ester consists of a mixture of methyl octanoate, methyl decanoate, methyl laurate and methyl myristate (ratio 7:8:64:21). C16/18 means that the methyl ester consists of a mixture of methyl palmitate ($C_{16}$-acyl radical) and methyl stearate ($C_{18}$-acyl radical) (ratio 30:70). C12/18 means that the methyl ester consists of a mixture of methyl laurate, methyl myristate, methyl palmitate, methyl stearate and methyl oleate (ratio 64:21:5:2:8).

TABLE 1

| Production example | Methyl ester | Active substance (%) | 1,2-Propylene glycol (%) | Melting point |
|---|---|---|---|---|
| H1 | C12/14 | 90 | 10 | 85 |
| H2 | C8/14 | 90 | 10 | 70 |
| H3 | C16/18 | 80 | 20 | 68 |
| H4 | C12/18 | 90 | 10 | 75 |

The viscosities were measured using a Brookfield viscometer model DV II and the spindles from the spindle set RV at 20 revolutions per minute and 20° C. The spindles 1 to 7 from the spindle set RV are used. Under these measurement conditions, spindle 1 is selected for viscosities of not more than 500 mPa·s, spindle 2 for viscosities of not more than 1000 mPa·s, spindle 3 for viscosities of not more than 5000 mPa·s, spindle 4 for viscosities of not more than 10 000 mPa·s, spindle 5 for viscosities of not more than 20 000 mPa·s, spindle 6 for viscosities of not more than 50 000 mPa·s and spindle 7 for viscosities of not more than 200 000 mPa·s.

Test Formulation:

Triglyceride oil-containing formulations were produced according to the following general formulation:

| Component A | Genapol ® LRO liquid (sodium lauryl ether sulfate) (27% solution in water, calculated on the basis of 100% active substance) | 7.2-9.6% by weight |
|---|---|---|
| Component D | Triglyceride oil | 0.2-0.6% by weight |
| Component B | Genagen ® CAB 818 (cocamidopropyl betaine) (30% solution in water, calculated on the basis of 100% active substance) | 2.4% by weight |
| Component E | Water | to 100.0% by weight |
| Component C | Sugar surfactant as per Production Examples H1-H3 | 2.67 or 3% by weight |
| Component F | Preservative (Nipaguard ® DMDMH) | 0.2% by weight |

(to 100.0 means making up to a total of 100.00% by weight, with the components C and F being included in the 100%).

Production:

Genapol® LRO liquid and triglyceride oil were mixed at 25° C. Water and cocamidopropyl betaine were added at 25° C. and the mixture was homogenized. Melted sugar surfactant was added, the mixture was homogenized at 75° C. and the viscosity was subsequently modified by addition of sodium chloride. The preservative was added after cooling to room temperature and the pH was brought to pH=5.5 by means of citric acid or NaOH. The appearance of the formulations was evaluated after 4 days.

All contents indicated are based on active content of the surfactant.

TABLE 2

| Example | Genapol ® LRO liquid (%) | Cocamidopropyl betaine (%) | Triglyceride oil | Proportion of triglyceride oil (%) | Sugar surfactant | Appearance of the formulation | NaCl addition (%) | Viscosity (mPas) |
|---|---|---|---|---|---|---|---|---|
| Comparative Example 1 | 9.6 | 2.4 | olive oil | 0.5 | — | white, turbid | 2.2 | 4750 |
| Comparative Example 2 | 7.2 | 2.4 | olive oil | 0.5 | cocoglucoside (Plantacare 818) | white, turbid | 2.5 | 7200 |
| 1 | 7.2 | 2.4 | olive oil | 0.5 | Production Example H1 | clear | 2.0 | 4700 |
| 2 | 7.2 | 2.4 | olive oil | 0.5 | Production Example H2 | clear | 2.8 | 5100 |
| 3 | 7.2 | 2.4 | olive oil | 0.5 | Production Example H3 | clear | 2.4 | 4900 |
| 4 | 7.2 | 2.4 | olive oil | 0.2 | Production Example H1 | clear | 1.9 | 4600 |
| 5 | 7.2 | 2.4 | sunflower oil | 0.4 | Production Example H1 | clear | 1.9 | 4750 |
| 6 | 7.2 | 2.4 | olive oil | 0.5 | Production Example H4 | clear | 1.6 | 5200 |

It can be seen from Examples 1-6 according to the invention that clear, thickenable, triglyceride oil-containing formulations can be obtained by use of the N-acyl-N-methylglucamines according to the invention. In contrast, clear formulations could not obtained without sugar surfactant (Comparative Example 1) or when using other sugar surfactants such as alkyl polyglucosides.

Analogous test formulations produced using silicone oil (Dimethicone 50 cSt) likewise did not give clear formulations.

The invention claimed is:

1. A clear composition containing:
   (A) at least one anionic surfactant as component A,
   (B) at least one betaine surfactant as component B,
   (C) at least one N-methyl-N-acylglucamine as component (C), where the N-methyl-N-acylglucamine has a $C_8$-$C_{22}$-acyl radical,
   (D) at least one unsaturated $C_8$-$C_{30}$ fatty acid triglyceride oil as component D,
   (E) at least one solvent as component E and
   (F) if desired one or more additives as component F.

2. The composition as claimed in claim 1, containing:
   (A) 5-15% by weight of component A,
   (B) 1-4% by weight of component B,
   (C) 0.5-5.0% by weight of component C,
   (D) 0.01-3.0% by weight of component D,
   (E) 5-93.49% by weight of a protic solvent as component E and
   (F) 0-10% by weight of component F,
   where the sum of the components A to F is 100% by weight.

3. The composition as claimed in claim 1, wherein component A is selected from the group consisting of compound(s) of the general formula (I),

where $R^1$ is alkyl, cycloalkyl, aralkyl, aryl, alkoxy, alkoxyalkyl or heterocyclyl and $M^+$ is an alkali metal ion, an alkaline earth metal ion or a substituted or unsubstituted ammonium ion, and
of the general formula (II),

where $R^1$ is alkyl, cycloalkyl, aralkyl, aryl, alkoxy, alkoxyalkyl or heterocyclyl and $M^+$ is an alkali metal ion, an alkaline earth metal ion or a substituted or unsubstituted ammonium ion.

4. The composition as claimed in claim 1, wherein the anionic surfactant of component A is an alkylsulfate or an alkyl ether sulfate.

5. The composition as claimed in claim 1, wherein component B comprises at least one alkyl betaine and/or at least one alkylamido betaine.

6. The composition as claimed in claim 1, wherein the acyl radical in component C is selected from the group consisting of linear, branched, saturated or unsaturated $C_8$-$C_{22}$-acyl radicals and mixtures thereof.

7. The composition as claimed in claim 1, wherein the sum of the components A, B and C is from 6.5 to 24% by weight.

8. The composition as claimed in claim 1, wherein component C consists of a saturated or unsaturated N-methyl-N-acylglucamine or a mixture of a plurality thereof.

9. The composition as claimed in claim 1, wherein the solvent is water or a mixture of water and propylene glycol.

10. The composition as claimed in claim 1, wherein the one or more additives are selected from the group consisting of preservatives, fragrances, dyes, further surfactants, water, oil bodies, cationic polymers, film formers, thickeners and gelling agents, oiling agents, antimicrobial and biogenic active compounds, moisture-donating agents, stabilizers, acids, alkalis, activity reinforcers and mixtures thereof.

11. A cosmetic, dermatological or pharmaceutical composition, comprising at least one clear composition as claimed in claim 1 and at least one customary cosmetic, dermatological or pharmaceutical additive.

12. A process for producing the composition as claimed in claim 1, comprising the steps of:
   a) mixing components A and D to form a mixture,
   b) adding components B and E to the mixture from step a), and subsequent homogenization of the components A, B, D and E to form a mixture,
   c) adding component C in liquid form to the mixture from step b) and subsequent homogenization of the components A, B, C, D and E,
   d) optionally adding component F and
   e) adjusting the pH of the composition to 5-8.

13. A shampoo, face cleanser, liquid cleanser or shower gel comprising at least one clear composition as claimed in claim 1 and at least one customary shampoo, face cleanser, liquid cleanser or shower gel additive.

14. A skin treatment or skin care product comprising at least one clear composition as claimed in claim 1 and at least one customary skin treatment or skin care product additive.

15. A hair treatment or hair care product comprising at least one clear composition as claimed in claim 1 and at least one customary hair treatment or hair care product additive.

* * * * *